US00PP09417P

United States Patent [19]

Hesse

[11] Patent Number: Plant 9,417

[45] Date of Patent: Jan. 2, 1996

[54] CHRYSANTHEMUM PLANT NAMED 'CANARY ISLE'

[75] Inventor: Peter S. Hesse, Nipomo, Calif.

[73] Assignee: Clearwater Nursery, Inc., Nipomo, Calif.

[21] Appl. No.: 422,444

[22] Filed: Mar. 31, 1995

[51] Int. Cl.[6] ..... A01H 5/00

[52] U.S. Cl. ..... Plt./82.2

[58] Field of Search ..... Plt./82.2

[56] References Cited

U.S. PATENT DOCUMENTS

P.P. 7,469 3/1991 VandenBerg ..... Plt./82.2

P.P. 8,474 11/1993 VandenBerg ..... Plt./82.2

*Primary Examiner*—Howard J. Locker

*Attorney, Agent, or Firm*—Arnold, White & Durkee

[57] ABSTRACT

The present invention comprises a new and distinct cultivar of Chrysanthemum, botanically known as *Dendranthema grandiflora*, and referred to by the cultivar name Canary Isle.

1 Drawing Sheet

BACKGROUND OF THE NEW PLANT

Canary Isle originated from a natural yellow mutation (sport) of the variety Icey Isle. This mutation was discovered by Peter S. Hesse growing in a controlled environment as one flowering shoot within a flowering bench of the proprietary seedling Icey Isle, in January of 1991. Icey Isle is the subject of U.S. Plant patent application Ser. No. 08/414,745, filed Mar. 31, 1995.

The first act of asexual reproduction of Canary Isle was accomplished in April 1991, when vegetative cuttings were taken in a controlled environment in Nipomo, Calif., by Peter S. Hesse. Horticultural examination of controlled flowerings of successive plantings has shown that the unique combination of characteristics as herein disclosed for Canary Isle are firmly fixed and are retained through successive generations of asexual reproduction.

Canary Isle has not been observed under all possible environmental conditions. The phenotype may vary significantly with variations in the environment such as temperature, light intensity and day length.

The following observations, measurements and comparisons describe plants grown in controlled environments at Clearwater Nursery, Nipomo, Calif. Unrooted cuttings were directly stuck into 6.5 inch pots and grown in a controlled environment under the natural temperature and day length prevailing in January to March.

The following traits have been repeatedly observed and are determined to be basic characteristics of Canary Isle which, in combination, distinguish this Chrysanthemum as a new and distinct cultivar.

1. Flat Capitulum Form.
2. Daisy Capitulum Type.
3. Yellow fully expanded outer ray florets.
4. Yellow Daisy disc with green eye.
5. A diameter of 12.5 cm across the face of the capitulum.
6. Exceptional upright to spreading habit with an average of 3.8 breaks after a single pinch.
7. Flowering response is approximately 58 days from the start of short days.
8. Relatively easy to control plant height from bench such that the finished height will range from 10 inches to 18 inches depending on pot size and market requirements.

DESCRIPTION OF THE PHOTOGRAPH

The accompanying photograph shows typical inflorescence and leaf characteristics of Canary Isle with the colors being as nearly true as possible with illustrations of this type. The photograph shows Canary Isle grown as a pinched spray pot mum with five (5) cuttings in a 6.5 inch pot.

DESCRIPTION OF THE PLANT

Of the commercial cultivars known to the inventor, the most similar in comparison to Canary Isle are the cultivars Splendor (U.S. Plant Pat. No. 5,225) and Hopscotch (U.S. Plant Pat. No. 5,816). Reference is made to Table I which compares certain characteristics of Canary Isle to the same characteristics of the above mentioned cultivars. The botanical information set forth for each cultivar below was observed from the cultivars when grown in a side-by-side relationship under controlled conditions in Nipomo, Calif. All color references and designations set forth in Table I and throughout the specification are from The Royal Horticultural Society (RHS) Colour Chart.

TABLE I

| CHARACTERISTIC | HOP-SCOTCH | CANARY ISLE | SPLENDOR |
|---|---|---|---|
| CAPITULUM FORMS | Flat | Flat | Flat |
| CAPITULUM TYPE | Daisy | Daisy | Daisy |
| DIAMETER ACROSS FACE | 7.5 cm | 12.5 cm | 12.2 cm |
| BRANCHING PATTERN | Upright Spreading | Upright Spreading | Upright Spreading |
| BREAKS/PINCH | 4.4 | 3.8 | 4.0 |
| HEIGHT IN 6.5" POT WITH 1–2 APPLICATIONS B-NINE ™ | 40–45 cm | 40–45 cm | 40–45 cm |
| RESPONSE: TREATMENT | 8.5 weeks medium vigorous grower | 8.5 weeks medium vigorous grower | 9.0 weeks medium vigorous grower |
| DISC FLORETS | | | |
| DISC FLORET COLOR | Yellow | Yellow | Yellow |
| NO. OF DISC FLORETS | 183.2 | 222.8 | 133.8 |
| LENGTH OF DISC FLORETS | 0.6 cm | 0.7 cm | 0.6 cm |
| RAY FLORETS | | | |
| COLOR | | | |
| FRONT: fully expanded | 9A Yellow | 4B Yellow | 75A Purple |
| FRONT: unfolded | 9A | 4B | 75A |

TABLE I-continued

| CHARACTERISTIC | HOP-SCOTCH | CANARY ISLE | SPLENDOR |
|---|---|---|---|
| ray florets | Yellow | Yellow | Purple |
| BACK: fully expanded | 6A | 4C | 75D |
| outer ray floret | Yellow | Yellow | Purple |
| NUMBER | 32.6 | 53.0 | 52.3 |
| SHAPE | Elliptic | Elliptic | Elliptic |
| LENGTH | 3.85 cm | 6.0 cm | 5.2 cm |
| WIDTH | 1.43 cm | 1.8 cm | 1.5 cm |
| TOTAL NUMBER OF FLOWERS/ BREAK | 6.7 | 7.6 | 10.4 |
| LEAF | | | |
| COLOR: | Front: 147A Back: 147B | Front: 147A Back: 147B | Front: 139A Back: 138A |
| MATURE LEAF LENGTH: | Up to 10.2 cm | Up to 8.5 cm | Up to 8.4 cm |
| MATURE LEAF WIDTH: | 5.95 cm | 5.2 cm | 4.5 cm |

Similar traits of the three cultivars include: The large flat, daisy capitulum. The diameter of the capitulum of Canary Isle tends to be as large as the capitulum of Splendor. Both Splendor and Canary Isle tend to have larger diameter capitulums than Hopscotch. All three cultivars have similar upright, spreading branching patterns and a similar number of breaks per pinch per plant. The finished plant height and the color of the disc florets is also similar for the three cultivars. Canary Isle tends to have more disc florets than either Hopscotch or Splendor. The length of the disc florets is also similar for the three cultivars. The front ray floret color of Canary Isle is yellow 4C, for Hopscotch is yellow 9A, and for Splendor is purple 75A. The back ray floret color of Canary Isle is yellow 4C, for Hopscotch yellow 6A, and for Splendor purple 75D. Canary Isle and Splendor have a similar number of ray florets. Hopscotch has the fewest number of ray florets. The ray florets of all three cultivars are elliptic. Splendor and Canary Isle have similar length ray florets. Both cultivars have longer ray florets than Hopscotch. The width of the ray florets is similar for all three cultivars. The color of the leaves of Canary Isle are similar to Hopscoth. Splendor has lighter leaves than either of the other cultivars. Hopscotch has the longest mature leaf length followed by Canary Isle, with Splendor having the shortest leaf. The three cultivars have similar leaf width. The response time from the start of short days is the same for Hopscotch and Canary Isle at 8.5 weeks. Response time is slightly longer for Splendor, 9.0 weeks.

THE PLANT

Classification:

*Botanical.*—*Dendranthema grandiflora.* Cultivar name: Canary Isle.

*Commercial.*—Flat daisy to be grown primarily as a Spray/CBR (central bud removed) or Disbud pot mum.

Inflorescence:

*Capitulum.*—Form: Flat. Type: Daisy. Diameter across face: 12.5 cm.

*Ray Florets.*—Color: Yellow (general tonality within a distance of three (3) meters). Front: Fully expanded ray floret 4B. Front: Unfolded ray florets in center of flower 4B. Back: Fully expanded outer ray floret 4C. Shape: Elliptic.

*Corolla of disc florets.*—Color: Edge begins with 14A to Center Green 141C.

Reproductive organs:

*Androecium.*—Present in disc floret; pollen: scant.

*Gynoecium.*—Present in both ray and disc floret.

General appearance:

*Height.*—When grown in a 6.5 inch pot with 1–4 applications of B-NINE™ at the rate of 2500 ppm, the total plant height from the bottom of the pot may be maintained at 40–45 cm. Branching Pattern: Upright and spreading with an average of 3.8 breaks when grown with one pinch.

*Foliage.*—Color: (upper surface) 147A. Color: (lower surface) 147B. Shape: (see photograph).

What is claimed is:

1. A new and distinct Chrysanthemum plant named Canary Isle substantially as herein described and shown, characterized by its yellow floret coloration and excellent upright spreading habit.

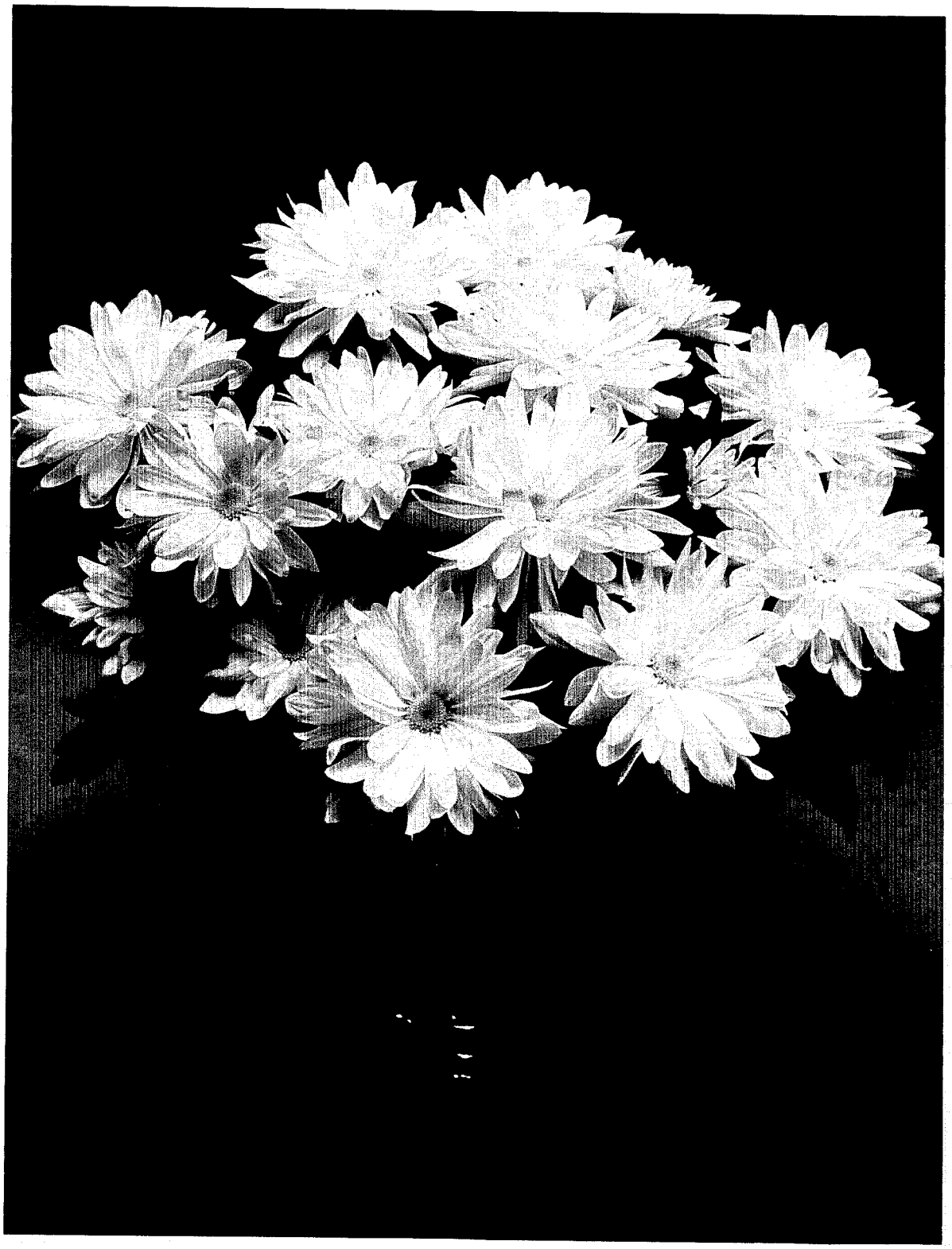

* * * * *